United States Patent
De et al.

(10) Patent No.: US 12,196,701 B2
(45) Date of Patent: Jan. 14, 2025

(54) SYSTEM AND METHOD FOR NON-INVASIVE ESTIMATION OF MILK QUALITY WITHIN TARGETED PACKAGING

(71) Applicant: Tata Consultancy Services Limited, Mumbai (IN)

(72) Inventors: Debankita De, Pune (IN); Parijat Dilip Deshpande, Pune (IN); Jayita Dutta, Pune (IN); Beena Rai, Pune (IN)

(73) Assignee: Tata Consultancy Services Limited, Mumbai (IN)

( * ) Notice: Subject to any disclaimer, the term of this patent is extended or adjusted under 35 U.S.C. 154(b) by 174 days.

(21) Appl. No.: 17/954,890

(22) Filed: Sep. 28, 2022

(65) Prior Publication Data

US 2023/0136868 A1   May 4, 2023

(30) Foreign Application Priority Data

Oct. 29, 2021  (IN) .............................. 202121049559

(51) Int. Cl.
  *G01N 27/22*  (2006.01)
  *G01N 33/04*  (2006.01)

(52) U.S. Cl.
  CPC .......... *G01N 27/221* (2013.01); *G01N 33/04* (2013.01)

(58) Field of Classification Search
  CPC .... G01N 27/221; G01N 33/04; G01N 27/226; G01N 27/22
  See application file for complete search history.

(56) References Cited

FOREIGN PATENT DOCUMENTS

| CN | 102680541 A | * | 9/2012 |
| JP | 2005-337986 A | | 12/2005 |
| WO | WO 2010/142301 A1 | | 12/2010 |

OTHER PUBLICATIONS

English translation of CN 102680541 (Year: 2012).*
Regression and sparse regression methods for viscosity estimation of acid milk from it's SLS features (Year: 2012).*
Goswami et al., "Arduino-Based Milk Quality Monitoring System," *IJAEB*: 14(2):245-249 (2021).

(Continued)

*Primary Examiner* — Feba Pothen
(74) *Attorney, Agent, or Firm* — Finnegan, Henderson, Farabow, Garrett & Dunner, LLP (57) ABSTRACT

State of the art milk quality estimation techniques fail to determine quality of the milk non-invasively. This disclosure relates generally to a system and method for non-invasive estimation of milk quality within targeted packaging. A voltage signal is applied at a first capacitor plate amongst a plurality of capacitor plates placed on either side of a targeted packaging containing milk, wherein the targeted packaging is placed inside an electrode receptacle. The resulting voltage signal is measured at a second capacitor plate of the plurality of capacitor plates. A capacitance value is calculated from the measured voltage signal and a value of pH corresponding to the calculated capacitance value is then determined using a regression-based model. A correlation of the determined value of pH with one or more pre-defined quality indices is performed and the quality of milk within the targeted packaging estimated based on the correlation.

12 Claims, 9 Drawing Sheets

(56) References Cited

OTHER PUBLICATIONS

Lu et al., "Milk Spoilage: Methods and Practices of Detecting Milk Quality," Food and Nutrition Sciences, 4:113-123 (2013).
Worku et al., "Detection of Adulteration in milk using capacitor sensor with especially focusing on Electrical properties of the milk," *Proceedings*, 4 (2020).

* cited by examiner

SYSTEM AND METHOD FOR NON-INVASIVE ESTIMATION OF MILK QUALITY WITHIN TARGETED PACKAGING

PRIORITY CLAIM

This U.S. patent application claims priority under 35 U.S.C. § 119 to: Indian Patent Application No. 202121049559, filed on Oct. 29, 2021. The entire contents of the aforementioned application are incorporated herein by reference.

TECHNICAL FIELD

The disclosure herein generally relates to milk quality estimation, and, more particularly, to a system and method for non-invasive estimation of milk quality within targeted packaging.

BACKGROUND

Milk is a complex media, comprising water, carbohydrates in the form of sugar lactose, fat, proteins (mainly casein, with smaller concentrations of other proteins), and mineral salts which makes milk a complete diet. Unfortunately, because of its properties, milk has become an ideal breeding ground for microorganisms capable of spoiling the milk. Intake of spoiled milk can cause diseases and therefore puts a strain on the healthcare system. Monitoring the quality of milk is thus of paramount importance for ensuring food safety and human health.

Currently, use-by date printed on packaged milk is used to get an estimate of the milk quality. However, these are based on an elementary estimate of the shelf-life and prove inadequate if the milk carton is exposed to extremes of temperature and humidity while in transit from manufactures to retailers.

Some of the existing techniques monitor the quality of milk by determining the spoilage of milk using the change in the pH value of milk, wherein the change in pH value is indicated by a change in color of the indicator. However, most of these techniques do not detect or monitor the quality of milk non-invasively. For example, one of the existing techniques monitors the quality of milk in real-time contained within a container, wherein the author has demonstrated the use of commercially available radio frequency identification (RFID) tags to monitor milk freshness. The sensor, which is attached to the side walls of the milk carton, detects the changes in the dielectric properties of the milk occurring due to the spoilage of milk. The sensor response is read by a pickup coil. The disadvantage of this being the presence of any metal layer in the packaging interferes with the measurement.

All of the aforementioned existing techniques however suffer from certain disadvantages which limit their practical use. Some of the techniques require elaborate laboratory setup, sample preparation steps, need for trained professional to interpret the test results, time consuming procedures, need to maintain stringent environmental conditions like temperature, etc. Further, there are certain techniques which are destructive in nature.

SUMMARY

Embodiments of the present disclosure present technological improvements as solutions to one or more of the above-mentioned technical problems recognized by the inventors in conventional systems. For example, in one embodiment, a method for non-invasive estimation of milk quality within targeted packaging is provided. The method includes applying, via one or more hardware processors, a voltage signal to a first capacitor plate amongst a plurality of capacitor plates placed on either side of a targeted packaging containing milk, wherein the targeted packaging is placed inside an electrode receptacle; measuring, via the one or more hardware processors, a resulting voltage signal at a second capacitor plate of the plurality of capacitor plates, wherein the resulting voltage signal at the second capacitor plate is due to one or more dielectric properties of the targeted packaging and the milk contained within the targeted packaging; calculating, via the one or more hardware processors, a capacitance value $C_T$ from the measured resulting voltage signal; determining, via the one or more hardware processors, a pH value corresponding to the calculated capacitance value $C_T$ based on one or more regression parameters comprised in a trained regression-based model; performing, via the one or more hardware processors, a correlation of the determined value of pH with one or more pre-defined quality indices; and estimating, via one or more hardware processors, the quality of milk within the targeted packaging based on the correlation.

In another aspect, there is provided a system for non-invasive estimation of milk quality within targeted packaging. The system comprises: a memory storing instructions; one or more communication interfaces; and one or more hardware processors coupled to the memory via the one or more communication interfaces, wherein the one or more hardware processors are configured by the instructions to: apply, a voltage signal to a first capacitor plate amongst a plurality of capacitor plates placed on either side of a targeted packaging containing milk, wherein the targeted packaging is placed inside an electrode receptacle. The system further comprises measuring a resulting voltage signal at a second capacitor plate of the plurality of capacitor plates, wherein the resulting voltage signal at the second capacitor plate is due to one or more dielectric properties of the targeted packaging and the milk contained within the targeted packaging; calculating, a capacitance value $C_T$ from the measured resulting voltage signal; determining a pH value corresponding to the calculated capacitance value $C_T$ based on one or more regression parameters comprised in a trained regression-based model; performing a correlation of the determined value of pH with one or more pre-defined quality indices; and estimating the quality of milk within the targeted packaging based on the correlation.

In yet another aspect, there are provided one or more non-transitory machine-readable information storage mediums comprising one or more instructions which when executed by one or more hardware processors cause applying a voltage signal to a first capacitor plate amongst a plurality of capacitor plates placed on either side of a targeted packaging containing milk, wherein the targeted packaging is placed inside an electrode receptacle; measuring a resulting voltage signal at a second capacitor plate of the plurality of capacitor plates, wherein the resulting voltage signal at the second capacitor plate is due to one or more dielectric properties of the targeted packaging and the milk contained within the targeted packaging; calculating, a capacitance value $C_T$ from the measured resulting voltage signal; determining a pH value corresponding to the calculated capacitance value $C_T$ based on one or more regression parameters comprised in a trained regression-based model; performing a correlation of the determined value of pH with one or more pre-defined quality indices; and estimating the quality of milk within the targeted packaging based on the correlation.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments.

Various embodiments disclosed herein provides method and apparatus for quality estimation of milk contained in a targeted packaging in a non-invasive manner. For example, in an embodiment, the disclosed apparatus includes a targeted packaging containing milk placed inside an electrode receptacle. A voltage signal is applied at one of the two capacitor plates placed on either sides of the targeted packaging and the resulting voltage signal is measured at other capacitor plate of the two capacitor plates. A capacitance value is calculated from the measured voltage signal and a value of pH corresponding to the calculated capacitance value is then determined using a regression-based model. The quality of milk is estimated by correlating the determined value of pH with the quality of the milk contained inside the targeted packaging.

Referring now to the drawings, and more particularly to FIG. 1 through FIG. 7, where similar reference characters denote corresponding features consistently throughout the figures, there are shown preferred embodiments and these embodiments are described in the context of the following exemplary system and/or method.

Figure 1:
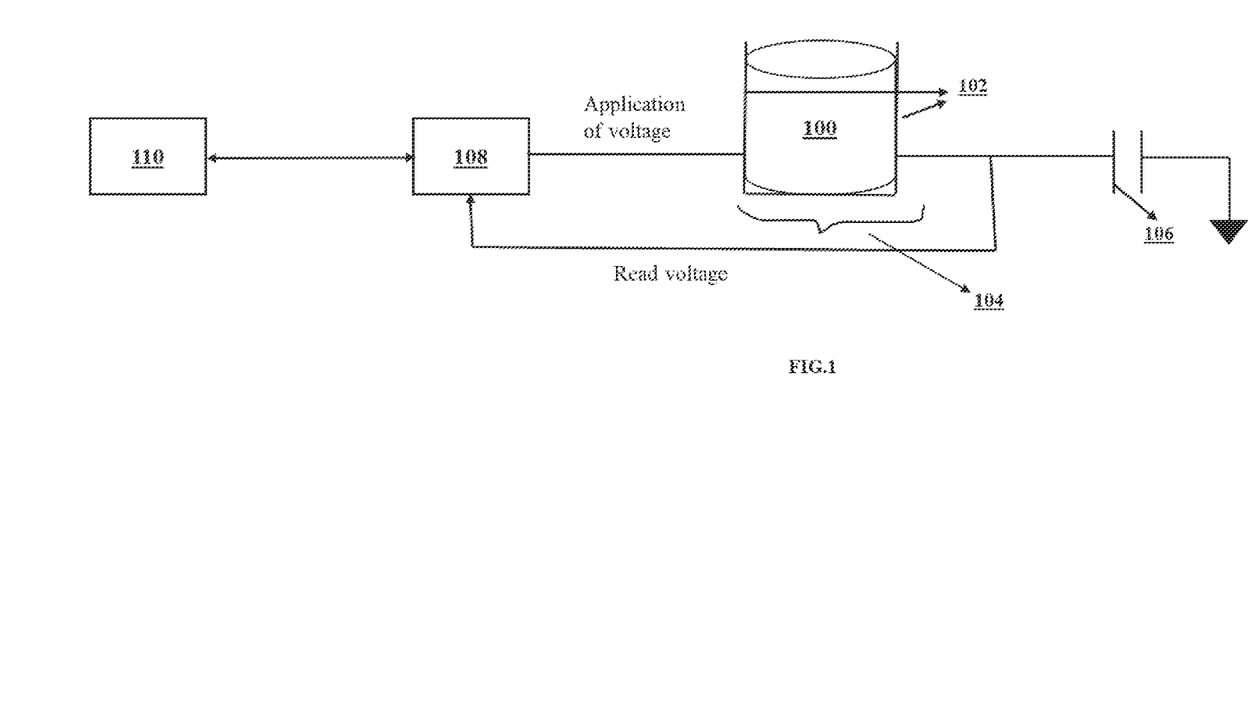
FIG. 1 illustrates an example of a targeted packaging for milk in accordance with an example embodiment of the present disclosure.

FIG. 1 illustrates an example of a targeted packaging for milk in accordance with an example embodiment of the present disclosure. For the brevity of description, the targeted packaging 100 is shown to assume a cylindrical shape, however it will be understood that the targeted packaging 100 may be of any shape other than the shape and size shown. The expression "targeted packaging" may also be referred as a container, for example Polyethylene terephthalate (PET) bottle, pouch, and the like, to hold milk for which the quality is determined.

In an embodiment of the present disclosure, the quality of milk contained inside the targeted packaging 100 is determined by monitoring the pH and capacitance of the milk sample. The targeted packaging 100 containing milk is placed in an Electrode receptacle 104 which enables the measurement of capacitance $C_T$ non-invasively and non-intrusively wherein the capacitance $C_T$ is used for estimation of quality of milk contained inside the targeted packaging 100 which is explained in the later sections. The two capacitor plates 102 (also referred as a first capacitor plate and a second capacitor plate) are placed on either side of the targeted packaging 100 wherein a voltage signal is applied through one of the two capacitor plates 102 through a microcontroller or a microprocessor 108. In an embodiment of the present disclosure, the microcontroller or the microprocessor 108 is configured to apply the voltage signal at the first capacitor plate of the two capacitor plates 102, measure the resulting voltage signal at the second capacitor plate of the two capacitor plates 102 and from the resulting voltage signal, the capacitance $C_T$ is captured or measured using the designed electrode receptacle 104 as depicted in FIG. 1. The voltage signal at the second capacitor plate is resulted due to the dielectric properties of the targeted packaging and the milk contained within the targeted packaging.

Figure 4A:
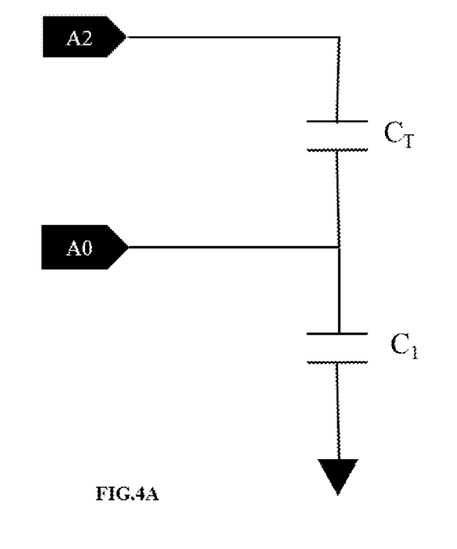
FIGS. 4A and 4B illustrate operation of capacitance measurement and an Arduino circuit (known in prior art) to measure capacitance respectively according to some embodiments of the present disclosure.
Figure 4B:
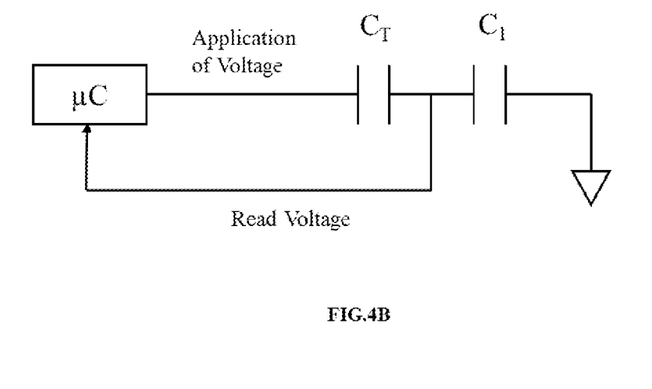

In an embodiment, the electrode receptacle 104 is assembled using a plurality of metal plates of regular dimensions (also referred as one or more pre-defined dimensions and interchangeably used herein) and a supporting material. Herein, the plurality of metal plates of regular dimensions can be Aluminium sheets and the supporting material can be a cardboard box. For example, the electrode receptacle 104 is assembled in a cardboard box using Aluminium sheets of dimension 4.5 cm×6 cm. Please note that the dimensions of the cardboard box and the Aluminium sheets may be customized according to the targeted packaging 100. Further, the dimension of the electrode receptacle 104 is based on the dimension and a form factor of the targeted packaging containing milk. Herein, the form factor refers to a physical form of the targeted packaging containing milk. For e.g., one PET bottle may be tall and cylindrical in shape and other PET bottle may be of different shape. In an embodiment of the present disclosure, to measure the capacitance $C_T$ a capacitive voltage divider circuit is built using an Arduino Uno (known in the art). The capacitive voltage divider circuit includes a reference capacitor $C_1$ 106 and the capacitance $C_T$, wherein the microcontroller or the microprocessor 108 is used to apply the voltage signal as depicted in FIGS. 4A and 4B. The reference capacitor $C_1$ 106 is used to complete the capacitive voltage divider circuit and to calibrate the measurement range of the capacitive voltage divider circuit.

In an embodiment of the present disclosure, a computing device 110 is configured to provide insights on the quality of milk contained inside the targeted packaging 100 based on the regression-based model embedded in the computing device 110. In an embodiment, the computing device 110 can include a laptop, a desktop or any computing device with a display unit. In another embodiment, the computing device 110 can be a composite system which includes the functionalities of both the computing device 110 and the microcontroller or the microprocessor 108.

Figure 2:
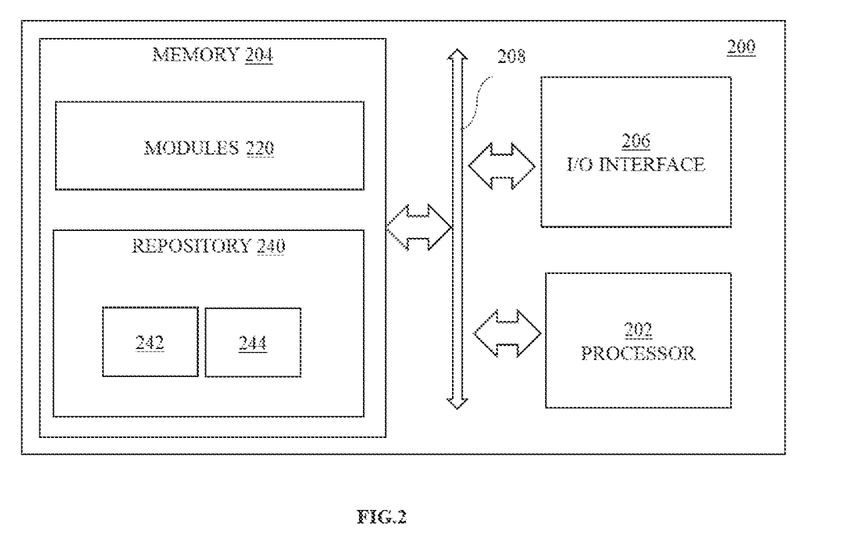
FIG. 2 illustrates a block diagram of a system for estimating quality of a milk contained in a targeted packaging (of FIG. 1), according to some embodiments of the present disclosure.

FIG. 2 illustrates a block diagram of a system for estimating quality of milk contained in a targeted packaging (of FIG. 1), according to some embodiments of the present disclosure. The system 200 is capable of training a model for estimating the quality of milk based on the changes in the capacitance value and pH value over a period of time.

The system 200 includes or is otherwise in communication with one or more hardware processors such as a processor 202, at least one memory such as a memory 204, and an I/O interface 206. The processor 202, memory 204, and the I/O interface 206 may be coupled by a system bus such as a system bus 208 or a similar mechanism. The I/O interface 206 may include a variety of software and hardware interfaces, for example, a web interface, a graphical user interface, and the like. The interfaces 206 may include a variety of software and hardware interfaces, for example, interfaces for peripheral device(s), such as a keyboard, a mouse, an external memory, a camera device, and a printer. Further, the interfaces 206 may enable the system 200 to communicate with other devices, such as web servers and external databases. The interfaces 206 can facilitate multiple communications within a wide variety of networks and protocol types, including wired networks, for example, local area network (LAN), cable, etc., and wireless networks, such as Wireless LAN (WLAN), cellular, or satellite. For the purpose, the interfaces 206 may include one or more ports for connecting a number of computing systems with one another or to another server computer. The I/O interface 206 may include one or more ports for connecting a number of devices to one another or to another server.

The hardware processor 202 may be implemented as one or more microprocessors, microcomputers, microcontrollers, digital signal processors, central processing units, state machines, logic circuitries, and/or any devices that manipulate signals based on operational instructions. Among other capabilities, the hardware processor 202 is configured to fetch and execute computer-readable instructions stored in the memory 204.

The memory 204 may include any computer-readable medium known in the art including, for example, volatile memory, such as static random-access memory (SRAM) and dynamic random-access memory (DRAM), and/or non-volatile memory, such as read only memory (ROM), erasable programmable ROM, flash memories, hard disks, optical disks, and magnetic tapes. In an embodiment, the memory 204 includes a plurality of modules 220 and a repository 240 for storing data processed, received, and generated by one or more of the modules 220. The modules 220 may include routines, programs, objects, components, data structures, and so on, which perform particular tasks or implement particular abstract data types.

The repository 240, amongst other things, includes a system database 242 and other data 244. The other data 244 may include data generated as a result of the execution of one or more modules in the other modules 220. In an embodiment, the repository 240 may store the data from the regression model of the capacitance and the associated pH value. The repository 240 may retrieve the pH value corresponding to the received measured capacitance $C_T$ associated with the estimation of quality of milk contained in the targeted packaging 100. A method of quality estimation of milk contained in the targeted packaging (for example, the targeted packaging 100) by using the system (for example, the system 200) is described further with reference to FIGS. 3A and 3B.

Figure 3A:
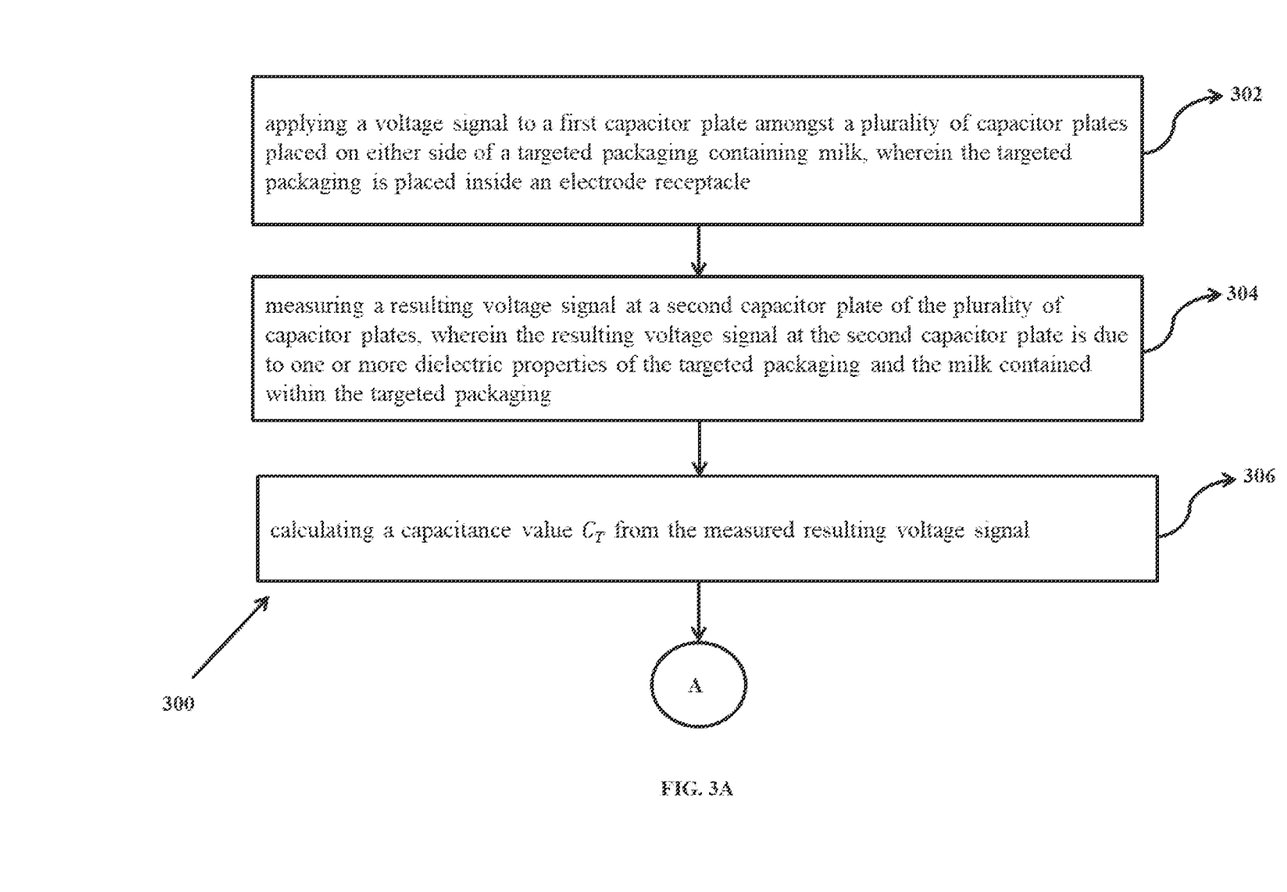
FIGS. 3A and 3B illustrates a method for estimating quality of milk contained in a targeted packaging in accordance with some embodiments of the present disclosure.
Figure 3B:
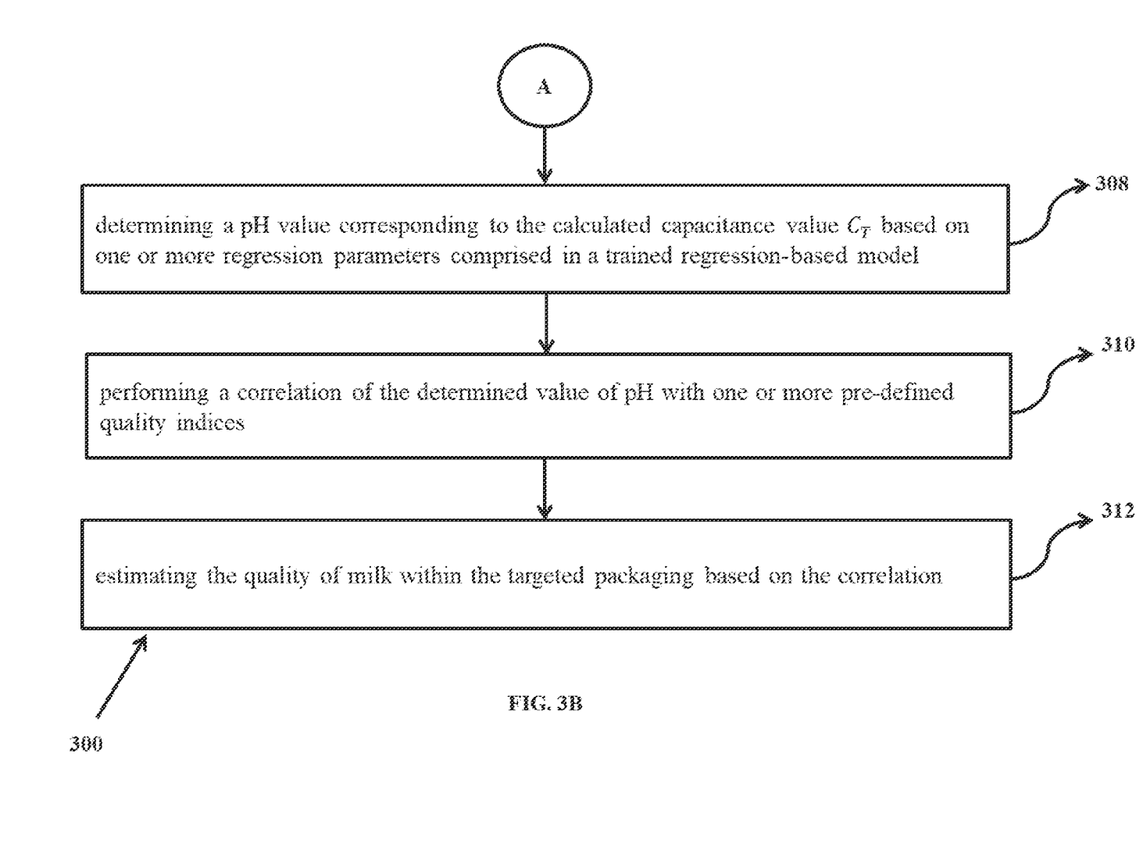

FIGS. 3A and 3B illustrate a method for estimating quality of milk contained in a targeted packaging in accordance with some embodiments of the present disclosure. The method 300 depicted in the flow chart may be executed by a system, for example, the system, 200 of FIG. 2. In an example embodiment, the system 200 may be embodied in a computing device, as will be described further in the description.

Operations of the flowchart, and combinations of operation in the flowchart, may be implemented by various means, such as hardware, firmware, processor, circuitry and/or other device associated with execution of software including one or more computer program instructions. For example, one or more of the procedures described in various embodiments may be embodied by computer program instructions. In an example embodiment, the computer program instructions, which embody the procedures, described in various embodiments may be stored by at least one memory device of a system and executed by at least one processor in the system. Any such computer program instructions may be loaded onto a computer or other programmable system (for example, hardware) to produce a machine, such that the resulting computer or other programmable system embody means for implementing the operations specified in the flowchart. It will be noted herein that the operations of the method 300 are described with help of system 200. However, the operations of the method 300 can be described and/or practiced by using any other system.

At 302 of the method 300, the one or more hardware processors 104 apply, a voltage signal to the first capacitor plate amongst a plurality of capacitor plates placed on either side of a targeted packaging (for example, the targeted packaging 100) containing milk, wherein the targeted packaging is placed inside an electrode receptacle. At 304 of the method 300, the one or more hardware processors 104 measure, a resulting voltage signal at the second capacitor plate of the plurality of capacitor plates, wherein the resulting voltage signal at the second capacitor plate is due to one or more dielectric properties of the targeted packaging and the milk contained within the targeted packaging. At 306 of the method 300, the one or more hardware processors 104 calculate, a capacitance value $C_T$ from the measured resulting voltage signal. At 308 of the method 300, the one or more hardware processors 104 determine, a pH value corresponding to the calculated capacitance value $C_T$ based on one or more regression parameters comprised in a trained regression-based model. At 310 of the method 300, the one or more hardware processors 104 perform, a correlation of the determined value of pH with one or more pre-defined quality indices. At 312 of the method 300, the one or more hardware processors 104 estimate, the quality of milk within the targeted packaging based on the correlation.

FIGS. 4A and 4B illustrate operation of capacitance measurement and an Arduino circuit (known in prior art) to measure capacitance respectively according to some embodiments of the present disclosure. In an embodiment of the present disclosure, the capacitance is measured using a capacitive voltage divider circuit which is built using an Arduino Uno (known in the art). The capacitive voltage divider circuit comprises of a reference capacitor $C_1$ and the capacitance $C_T$. The voltage signal at one of the two capacitor plates, $V_{A2}$ is modified/changed (e.g., increase in values or decrease in values) to 'x' volts (e.g., 5V as per experiments conducted) and the voltage signal at the other capacitor plate of the two capacitor plates, $V_{A0}$ is measured, wherein the microcontroller or the microprocessor 108 is used to apply the voltage signal as depicted in FIGS. 4A and 4B. Such values of voltage signal shall not be construed as limiting the scope of the present disclosure. The following formulae or equation is used to calculate the capacitance $C_T$:

$$C_T = \frac{V_{A0}C_1}{(V_{A2} - V_{A0})}$$

Figure 5A:
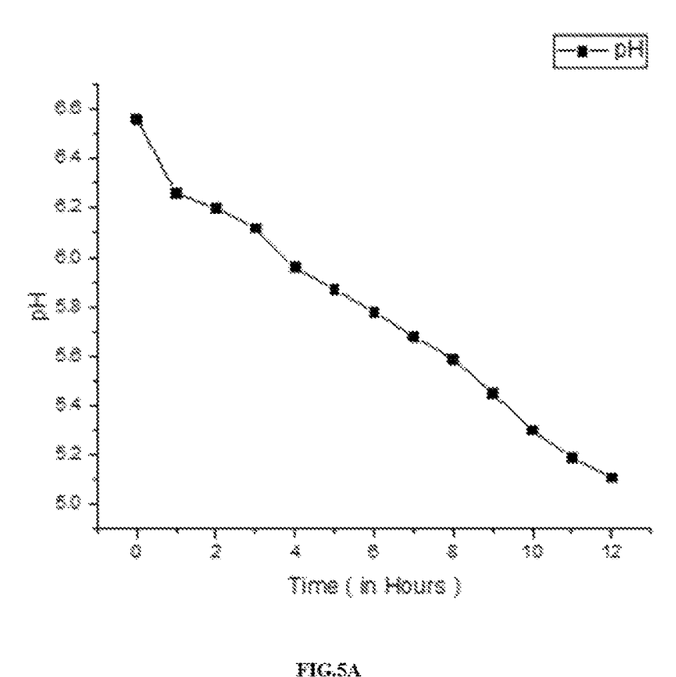
FIGS. 5A and 5B show an example illustrating a change in a pH and a capacitance value respectively in accordance with some embodiments of the present disclosure.
Figure 5B:
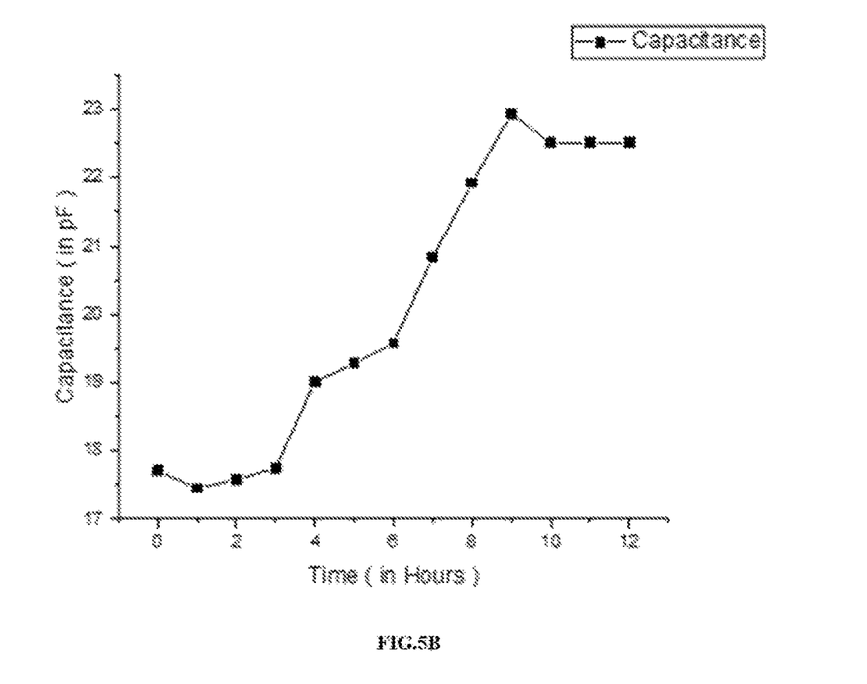

FIGS. 5A and 5B show an example illustrating a change in a pH and a capacitance value respectively in accordance with some embodiments of the present disclosure. In an embodiment of the present disclosure, the regression-based model is used to study the correlation between the pH and capacitance. For example, when milk is kept at a room temperature (around 30° C.), the milk takes around 8 to 10 hours to be rendered as unconsumable. With time, a rising trend in the capacitance is observed. From this observation, it can be said that the dielectric constant, which is a physical parameter of the milk also rises with time. Further, the dielectric constant may be derived from the calculated capacitance values using an equation $$C_T = \frac{\varepsilon_0 A}{d}$$

where $C_T$ is the calculated capacitance value, $\varepsilon_0$ is the dielectric constant of milk, A is the area of the capacitor plates and d is the distance between the two capacitor plates. Representative plots illustrating the trends in the change in the capacitance and the pH over time are illustrated in FIGS. 5A and 5B.

Figure 6:
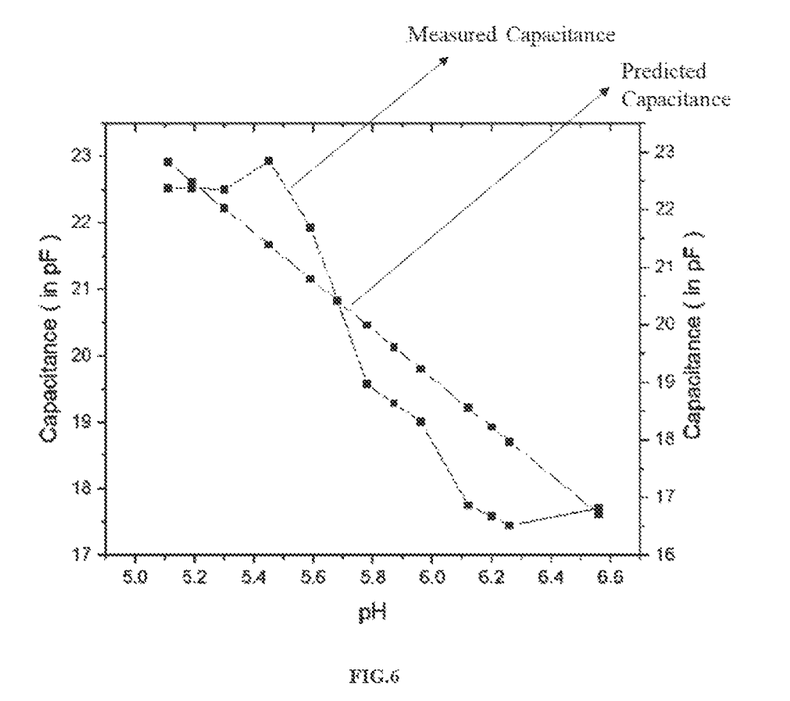
FIG. 6 depicts a use case example illustrating the relationship between the capacitance (actual and predicted) and the pH in accordance with some embodiments of the present disclosure.

FIG. 6 depicts a use case example illustrating the relationship between the capacitance (actual and predicted) and the pH in accordance with some embodiments of the present disclosure. A plot illustrating the overlap of the measured/actual and predicted values of capacitance and the pH is depicted in FIG. 6. As discussed above, the regression analysis or the regression-based model is used to study the relationship between the capacitance and pH value. Referring to FIG. 6, for one of the representative plots, it is found that the pH and the capacitance exhibit a correlation coefficient of 0.9414 which is very near to 1 and this indicates a strong positive relationship between the pH and the capacitance. A significance-F value of $1.59 \times 10^{-6}$ which is a parameter of the regression-based model indicates that the relationship is statistically significant.

Figure 7:
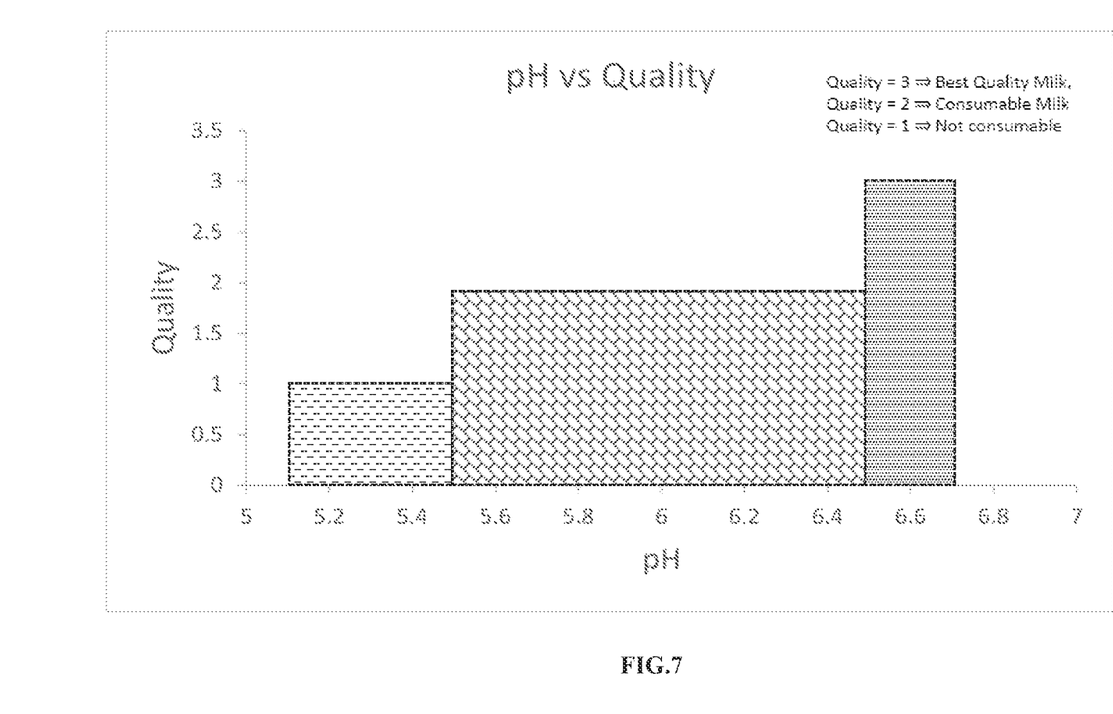
FIG. 7 illustrates a use case example for estimating the quality of milk by correlating a pH value with the quality of the milk contained inside the targeted packaging in accordance with some embodiments of the present disclosure.

FIG. 7 illustrates a use case example for estimating the quality of milk by correlating a pH value with the quality of the milk contained inside the targeted packaging in accordance with some embodiments of the present disclosure. The pH is a widely accepted indicator of milk quality, with the pH of perfectly good milk being in the range of 6.5-6.7 (as known in the prior art). In an embodiment of the present disclosure, quality of milk contained inside the targeted packaging 100 is estimated by correlating the pH value with the quality of the milk. For example, quality value=3 indicates that the milk is of best quality, which is ideal for consumption, quality value=2 indicates the consumable milk, quality value=1 indicates the non-consumable milk which means the milk is spoiled or not ideal for consumption as depicted in FIG. 7.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

Various embodiments disclosed herein provide system and method for non-invasive estimation of milk quality within targeted packaging. The embodiment of the present disclosure herein addresses unresolved problem of monitoring and estimation of milk non-invasively based on capacitive changes in milk using a customized electrode receptacle. A regression-based model is developed using the data obtained by capturing the change in capacitance and pH values over time to estimate the quality of milk.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g., any kind of computer like a server or a personal computer, or the like, or any combination thereof. The device may also include means which could be e.g., hardware means like e.g., an application-specific integrated circuit (ASIC), a field-programmable gate array (FPGA), or a combination of hardware and software means, e.g., an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g., using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method, comprising:
   applying, via one or more hardware processors, a voltage signal to a first capacitor plate amongst a plurality of capacitor plates placed on either side of a targeted packaging containing milk, wherein the targeted packaging is placed inside an electrode receptacle;
   measuring, via the one or more hardware processors, a resulting voltage signal at a second capacitor plate of the plurality of capacitor plates, wherein the resulting voltage signal at the second capacitor plate is due to one or more dielectric properties of the targeted packaging and the milk contained within the targeted packaging;
   calculating, via the one or more hardware processors, a capacitance value $C_T$ from the measured resulting voltage signal;
   determining, via the one or more hardware processors, a pH value corresponding to the calculated capacitance value $C_T$ based on one or more regression parameters comprised in a trained regression-based model, wherein the one or more regression parameters comprise a correlation coefficient, a significance-F value, wherein the significance-F value indicating a relationship between the pH value and the capacitance value $C_T$ is statistically significant, and the pH value and the capacitance value $C_T$ exhibit a correlation coefficient of 0.9414 indicating relationship between the pH value and the capacitance value $C_T$, wherein the capacitance value $C_T$ and the associated pH value is stored in a repository;
   performing, via the one or more hardware, a correlation of the determined value of pH with one or more pre-defined quality indices; and
   estimating, via one or more hardware processors, the quality of milk within the targeted packaging based on the correlation.

2. The processor implemented method of claim 1, wherein the electrode receptacle is assembled using a plurality of metal plates of one or more pre-defined dimensions and a supporting material.

3. The processor implemented method of claim 2, wherein a dimension of the electrode receptacle is based on a dimension and a form factor of the targeted packaging containing milk.

4. The processor implemented method of claim 1, wherein the one or more regression parameters further include a R-square value.

5. A system, comprising:
   a memory storing instructions;
   one or more communication interfaces; and
   one or more hardware processors coupled to the memory via the one or more communication interfaces, wherein the one or more hardware processors are configured by the instructions to:
      apply, a voltage signal to a first capacitor plate amongst a plurality of capacitor plates placed on either side of a targeted packaging containing milk, wherein the targeted packaging is placed inside an electrode receptacle;
      measure, a resulting voltage signal at a second capacitor plate of the plurality of capacitor plates, wherein the resulting voltage signal at the second capacitor plate is due to one or more dielectric properties of the targeted packaging and the milk contained within the targeted packaging;
      calculate, a capacitance value $C_T$ from the measured resulting voltage signal;
      determine, a pH value corresponding to the calculated capacitance value $C_T$ based on one or more regression parameters comprised in a trained regression-based model, wherein the one or more regression parameters comprise a correlation coefficient, a significance-F value, wherein the significance-F value indicating a relationship between the pH value and the capacitance value $C_T$ is statistically significant, and the pH value and the capacitance value $C_T$ exhibit a correlation coefficient of 0.9414 indicating relationship between the pH value and the capacitance value $C_T$, wherein the capacitance value $C_T$ and the associated pH value is stored in a repository;
      perform, a correlation of the determined value of pH with one or more pre-defined quality indices; and
      estimate, the quality of milk within the targeted packaging based on the correlation.

6. The system of claim 5, wherein the electrode receptacle is assembled using a plurality of metal plates of one or more pre-defined dimensions and a supporting material.

7. The system of claim 6, wherein a dimension of the electrode receptacle is based on a dimension and a form factor of the targeted packaging containing milk.

8. The system of claim 5, wherein the one or more regression parameters further include a R-square value.

9. One or more non-transitory machine-readable information storage mediums comprising one or more instructions which when executed by one or more hardware processors cause:
   applying a voltage signal to a first capacitor plate amongst a plurality of capacitor plates placed on either side of a targeted packaging containing milk, wherein the targeted packaging is placed inside an electrode receptacle;
   measuring a resulting voltage signal at a second capacitor plate of the plurality of capacitor plates, wherein the resulting voltage signal at the second capacitor plate is due to one or more dielectric properties of the targeted packaging and the milk contained within the targeted packaging;

calculating a capacitance value $C_T$ from the measured resulting voltage signal;

determining a pH value corresponding to the calculated capacitance value $C_T$ based on one or more regression parameters comprised in a trained regression-based model, wherein the one or more regression parameters comprise a correlation coefficient, a significance-F value, wherein the significance-F value indicating a relationship between the pH value and the capacitance value $C_T$ is statistically significant, and the pH value and the capacitance value $C_T$ exhibit a correlation coefficient of 0.9414 indicating relationship between the pH value and the capacitance value $C_T$, wherein the capacitance value $C_T$ and the associated pH value is stored in a repository;

performing a correlation of the determined value of pH with one or more pre-defined quality indices; and estimating the quality of milk within the targeted packaging based on the correlation.

10. The one or more non-transitory machine-readable information storage mediums of claim 9, wherein the electrode receptacle is assembled using a plurality of metal plates of one or more pre-defined dimensions and a supporting material.

11. The one or more non-transitory machine-readable information storage mediums of claim 10, wherein a dimension of the electrode receptacle is based on a dimension and a form factor of the targeted packaging containing milk.

12. The one or more non-transitory machine-readable information storage mediums of claim 9, wherein the one or more regression parameters further include a R-square value.

* * * * *